United States Patent [19]
Thead et al.

[11] Patent Number: 5,188,598
[45] Date of Patent: Feb. 23, 1993

[54] APPARATUS AND METHOD FOR SAFELY DISPOSING CONTAMINATED NEEDLES

[75] Inventors: William H. Thead; John C. Evans, both of Atlanta, Ga.

[73] Assignee: Post Medical, Inc., Atlanta, Ga.

[21] Appl. No.: 607,553

[22] Filed: Nov. 1, 1990

Related U.S. Application Data

[63] Continuation-in-part of Ser. No. 248,470, Sep. 23, 1988, Pat. No. 4,986,811.

[51] Int. Cl.$^5$ .............................................. A61M 5/32
[52] U.S. Cl. ..................................... 604/110; 206/366
[58] Field of Search ...................... 604/110, 192, 240; 206/366; 220/1 T, 905, 906

[56] References Cited

U.S. PATENT DOCUMENTS

| D. 287,897 | 1/1987 | Hanifl . | |
|---|---|---|---|
| 4,375,849 | 3/1983 | Hanifl . | |
| 4,667,821 | 5/1987 | Shillington . | |
| 4,798,587 | 1/1989 | Willoughby . | |
| 4,807,344 | 2/1989 | Kelson et al. . | |
| 4,862,573 | 9/1989 | Kelson et al. | 206/366 |
| 4,919,264 | 4/1990 | Shinall | 220/909 |
| 4,922,597 | 5/1990 | Ikeda et al. | 206/366 |
| 4,986,811 | 1/1991 | Thead et al. | 604/110 |
| 4,989,307 | 2/1991 | Sharpe et al. | 206/366 |
| 4,995,871 | 2/1991 | Sasaki et al. | 206/366 |

FOREIGN PATENT DOCUMENTS

2601512  3/1977  Fed. Rep. of Germany .

Primary Examiner—C. Fred Rosenbaum
Assistant Examiner—Chalin Smith
Attorney, Agent, or Firm—Jones & Askew

[57] ABSTRACT

A device for safely removing contaminated needles from syringes without exposing medical personnel to unnecessary health risks. The device requires only one hand to operate; medical personnel simply insert the syringe and press downwardly. The pressure exerted by the user causes disconnect gears to engage the collar of the needle and unscrew the needle from the syringe, at which time the needle falls into a container. The device includes means for forcing needles into the container when the rubber portion of an unscrewed needle gets "trapped" in the disconnect gears, and also includes means for preventing further disengagement of needles when the container cannot safely accommodate additional needles. Also included in the disclosed device is an opening for receiving needles other than the type that can be disconnected by the gears. The container includes a recess for storing a permanent lid, which is applied to the device when the container is full and ready to be disposed.

33 Claims, 10 Drawing Sheets

Fig_23 PRIOR ART

Fig_4

Fig_5

Fig_6

Fig_9

Fig_7

Fig_10

Fig_8

Fig_12

Fig_11

Fig_13

Fig_20   Fig_21

Fig_19

APPARATUS AND METHOD FOR SAFELY DISPOSING CONTAMINATED NEEDLES

CROSS-REFERENCE TO RELATED APPLICATION

This application is a continuation-in-part of Ser. No. 248,470, filed Sep. 23, 1988, now U.S. Pat. No. 4,986,811, issued Jan. 22, 1991.

TECHNICAL FIELD

The present invention relates to the disposal of blood contaminated needles attached using rotating connectors such as screw connectors or luer locks to syringes, and more particularly relates to an apparatus and method for removing such needles and depositing them into a container in a one-handed operation which greatly reduces the exposure of the user to being injured by the contaminated needle.

BACKGROUND ART

Each day, staggering quantities of disposable needles are used in hospitals, clinics, and physicians' offices. Many such needles are attached to syringes which are not discarded with the needles. For example, a syringe of the type sold under the trademark VACUTAINER is used by securing a double needle to a needle retainer by screwing a threaded collar on the needle into a threaded opening in the end of the needle retainer. After the needle point outside the needle retainer is inserted into the patient's vein, a partially evacuated sample tube is forced onto the other needle point inside the retainer, and blood is sucked into the sample tube. The sample tube is removed and sent for analysis of its contents, and the needle retainer may be reused. Therefore, medical personnel typically remove the needle by unscrewing it, and place the needle in an approved disposal container.

Other types of syringes also use disposable needles with non-disposal suction devices. The needles may be connected by threaded screw connectors, luer locks, or the like. Disposable needles are typically fitted with plastic collars which have flange-like projections suitable for grasping with the fingers when twisting the needle into or out of the needle retaining portion of a syringe.

Personnel at hospitals and other medical facilities face a growing problem of safe disposal of needles because of the rise of diseases carried by the blood and other bodily fluids, such as AIDS. Manipulation of needle connectors after use can present a grave risk of being pricked by the exposed, contaminated needle. Attempts to insert the needle back into the protective sleeve provided for shipment create a similar risk. Past efforts to assist personnel in removing needles have reduced the danger somewhat, but have resulted in devices that are inconvenient to use. One such device is simply a container having a tapering slot in the top. The user holds the needle retainer, inserts the needle into the slot until the flanges of the collar are even with the slot, moves the needle into the smaller end of the slot until the flanges engage the slot, and twists the needle retainer to unscrew or unlock the needle, which falls into the container. This procedure has significant disadvantages. The user must position the needle carefully and supply the force necessary to rotate the needle retainer. Usually, the user must use two hands for the operation, one to steady the container, and one to manipulate the syringe and needle. This often results in the user laying down the used syringe for a time until both hands are available for removing the needle, rather than immediately placing the needle into a safe container. These disadvantages increase the opportunity and risk that a person will come into contact with the contaminated needle.

A significant attempt to overcome the above-discussed disadvantages in prior needle removal systems is the subject of U.S. Ser. No. 248,470, now U.S. Pat. No. 4,986,811. However, this application fails to address a number of significant problems still present in the art. First, a problem exists when the container in which contaminated needles are disposed reaches a point where it can no longer safely receive contaminated needles. When the container reaches a certain accumulation point, it is possible for disposed needles to escape through the openings into which needles are placed within the container.

Additionally, a problem exists in that hospital personnel often handle needles other than the type attached to syringes. Rather than require a second disposal unit for such needles, a need exists in the art for a needle removal system which removes both types of needles. However, in order to accommodate disposal of non-syringe attached needles, an opening must be included in the cover of the needle removal system. Such an opening invites spillage of disposed needles in the event that the needle removal container is knocked out of its normal, upright position.

Also, a problem exists in that some types of needles include a rubber sleeve which terminates is an enlarged ring next to their threads. When these needles are unthreaded, this rubber ring has a tendency to become caught in the unthreading means, thus interfering with safe disposal of the needle.

Thus, a need exists in the art for a needle removal system which can remove the disposable needle from the syringe with minimal non-precise manipulation of the needle and syringe using only one hand.

In addition, a need exists in the art for a needle removal system which prevents removal of additional needles when the container holding disposed needles cannot safely receive further needles, and a need also exists in the art for permitting disposal of needles of the type not attached to syringes, in a manner that does not invite spillage of disposed needles if the needle removal container is knocked over. A need also exists for automatically separating a needle from a syringe after unthreading the needle from the syringe.

SUMMARY OF THE INVENTION

The present invention solves significant problems in the art by providing a needle removal apparatus and method according to which the user, touching only the needle retaining portion of the syringe, inserts the needle into a device which automatically rotates the needle to disconnect it from the syringe.

Generally described, the present invention provides an apparatus for removing needles of the type received in syringe bodies by way of a rotating connector, and defining a collar positioned outside the syringe body, comprising a carriage defining an insert opening for receiving the needle, and means for engaging the collar and rotating the needle, such that the needle is released from the syringe. In the preferred embodiment of the invention, the means for rotating the needle comprises at least one disconnect wheel rotatably mounted adjacent to the insert opening, the wheel defining means at its periphery, facing the insert opening, for engaging the needle collar; and means for rotating the disconnect wheel in a disconnect direction responsive to downward movement of the needle into the insert opening.

Many disposable needles include a plurality of flanges extending outwardly from the collar, and in this case the means for rotating the needle preferably comprises at least one disconnect gear rotatably mounted adjacent to the insert opening with teeth facing the insert opening, so that the needle flanges engage the gear teeth. The carriage may be mounted for movement within an actuator housing; and the means for rotating the gear may comprise a drive gear engaging the disconnect gear, with the drive gear defining a cam follower. A cam track is then positioned in the actuator housing to receive the cam follower and shaped so as to move the drive gear with respect to the disconnect gear as the carriage moves within the actuator housing responsive to pressure exerted on the needle.

A needle removal apparatus according to the invention preferably includes a container adjacent to the needle rotating means for confining needles removed from syringes.

The present invention also provides a means for disposal of certain needles other than those of the type received in syringe bodies by way of an opening in the top of the container in which the needles the received. The disposal means, in the present invention, includes a triangular opening, resembling a coat hanger, in the cover portion of the container. Hospital personnel may discard contaminated needles other than those attached to syringes, such as so-called butterfly needles, into this opening.

A needle removal apparatus according to another aspect of the invention preferably includes means responsive to an accumulation of a predetermined number of needles in the container for preventing disposal of additional needles. The preferred embodiment of the present invention provides a locking leg, mounted on the bottom of the needle housing, which prevents needles from escaping from the container via the insert opening. After a certain quantity of needles has been placed inside the container, the leg, when the needle housing is moved downward, will contact the pile of needles inside the container and, not being able to move further downward, will lock into a position which prevents further operation of the carriage.

The present invention also provides a method of removing a needle from a syringe body to which the needle is attached by a rotating connector, generally comprising the steps of inserting the needle into an opening in a housing and engaging the syringe body against the housing; exerting pressure against the housing; and responsive to the pressure, rotating the needle sufficiently to release the needle from the syringe body. The present invention also provides means to ensure that once the needle has been rotated sufficiently for release from the syringe, the needle will be completely urged away from the syringe and will drop into the container.

Thus, it is an object of the present invention to provide an improved apparatus and method of removing needles from syringes and the like.

It is a further object of the present invention to provide a needle removal system which can be operated using one hand.

It is a further object of the present invention to provide a needle removal system which does not require precise manipulation of the needle to achieve removal.

It is a further object of the present invention to provide a needle removal system which presents little danger to the user.

It is a further object of the present invention to provide a needle removal system which automatically urges a needle away from its syringe after the needle has been unthreaded.

It is a further object of the present invention to provide a needle removal system which can be used quickly and conveniently.

It is a further object of the present invention to provide a needle removal system which permits disposal of numerous types of needles, including those attached to a syringe.

It is a further object of the present invention to provide a needle removal system which prevents further removal of needles when the container into which the needles are removed cannot safely hold additional needles.

Other objects, features, and advantages of the present invention will become apparent upon reading the following detailed description of embodiments of the invention, when taken in conjunction with the accompanying drawing and the appended claims.

DETAILED DESCRIPTION

Figure 1:
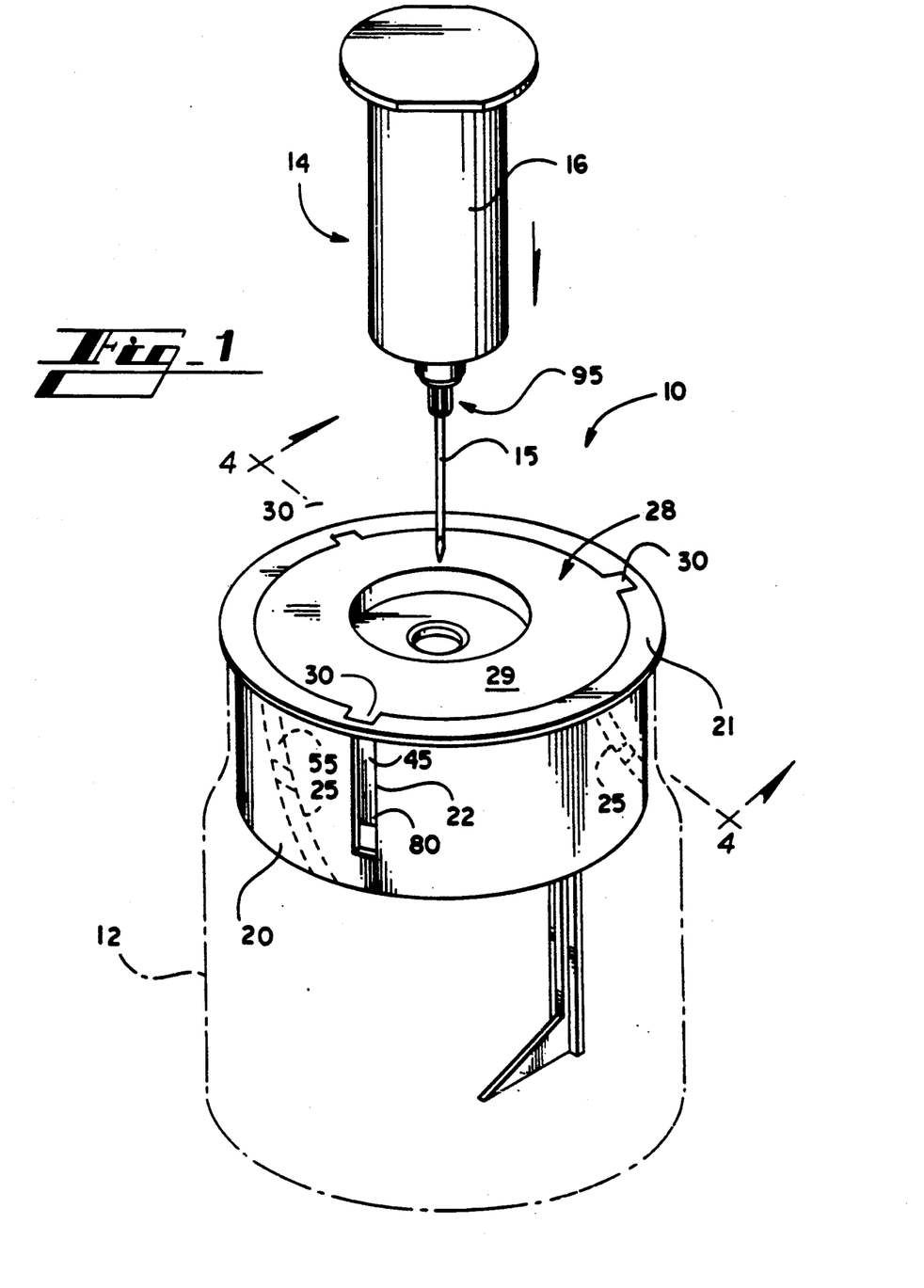
FIG. 1 is a pictorial view of a needle removal apparatus embodying the present invention with the cover removed.
Figure 22:
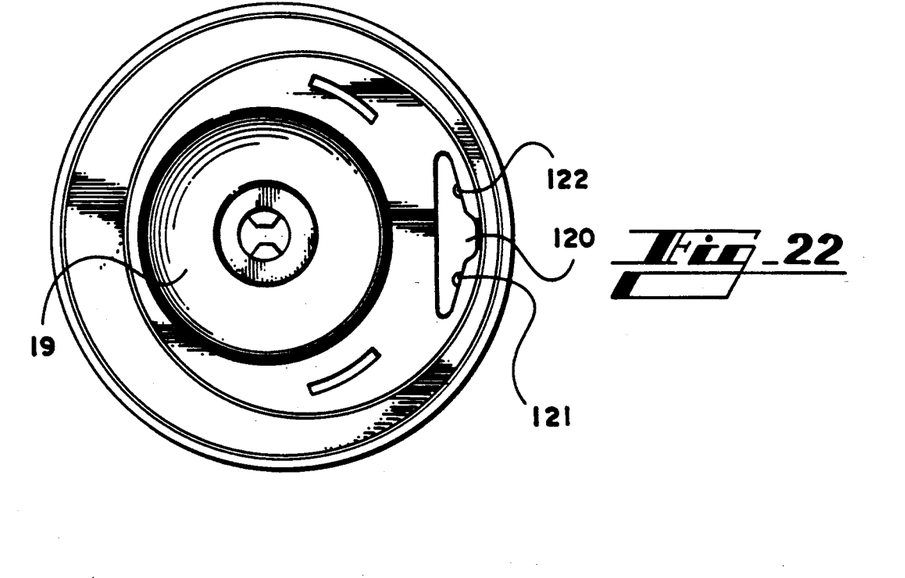
FIG. 22 is a top view of the cover of the needle removal apparatus, showing the coat hanger-like opening into which needles not attached to syringes are placed for disposal.

Referring now to the drawing, in which like numerals refer to like parts throughout the several views, FIG. 1 shows a needle removal apparatus 10 embodying the invention. The needle removal apparatus 10 is normally mounted in the mouth of a container 12, shown in dotted lines in FIG. 1, and protected by a cover 13, shown in FIGS. 4 and 22. The container 12 may be a glass or plastic jar, for example. A syringe assembly 14 is shown in a position prior to insertion in the needle removal apparatus 10, and includes a needle 15 and a needle retainer portion 16. When the assembly 14 is inserted in the direction of the arrow, the parts of the needle removal apparatus described below automatically disconnect the needle 15 from the retainer 16.

Figure 2:
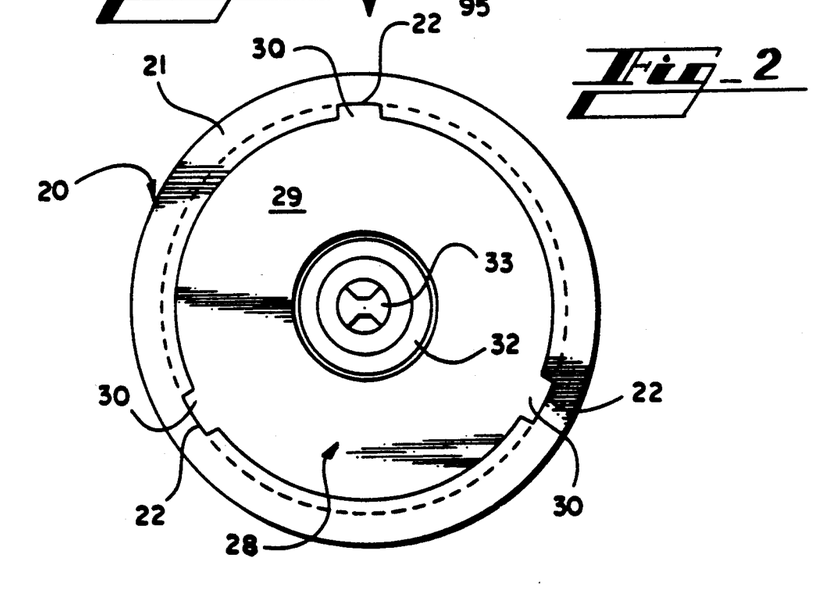
FIG. 2 is a top plan view of the apparatus shown in FIG. 1, with the cover removed.

Referring to FIGS. 1 and 2, the apparatus 10 includes an actuator housing 20, which is a cylinder open at both ends. Its top end is surrounded by an annular flange 21 which extends radially outwardly from the cylindrical wall. The housing 20 defines three vertical slots 22 which intersect the flange 21 and extend down to a point spaced above the bottom of the housing 20. The interior of the cylindrical wall defines three arcuate grooves 25 extending at an angle, preferably 40-60 degrees from the horizontal, from just under the flange 21 to the bottom of the housing 20. These grooves 25 form cam tracks or female screw threads to cause rotary motion, as described below.

Fitted for vertical motion within the actuator housing 20 is a carriage 28, which is formed having a horizontal annular plate 29. As shown in FIG. 2, three tabs 30 extend outwardly from the circumference of the annular plate 29 and enter the slots 22 of the actuator housing 20. The tabs 30 thus prevent the carriage 28 from rotating, but allow vertical movement. Slightly below the plane of the plate 29, a recessed annular shoulder 32 is formed around an insert opening 33, into which the needle 15 is placed. An annular portion 19, shown in FIG. 4, surrounding the opening 33 is provided in the cover 13 to help guide needles to the opening. A pair gear shafts 34 and 35 extend vertically downward on opposite sides of the insert opening 33. The shafts terminate in lock posts 37 and 38, which are somewhat smaller in diameter than the shafts 34 and 35. The carriage 28 also defines three spring stop tabs 40 which project downwardly near the periphery of the annular plate 29. The tabs 40 are spaced evenly around the plate 29.

Figure 3:
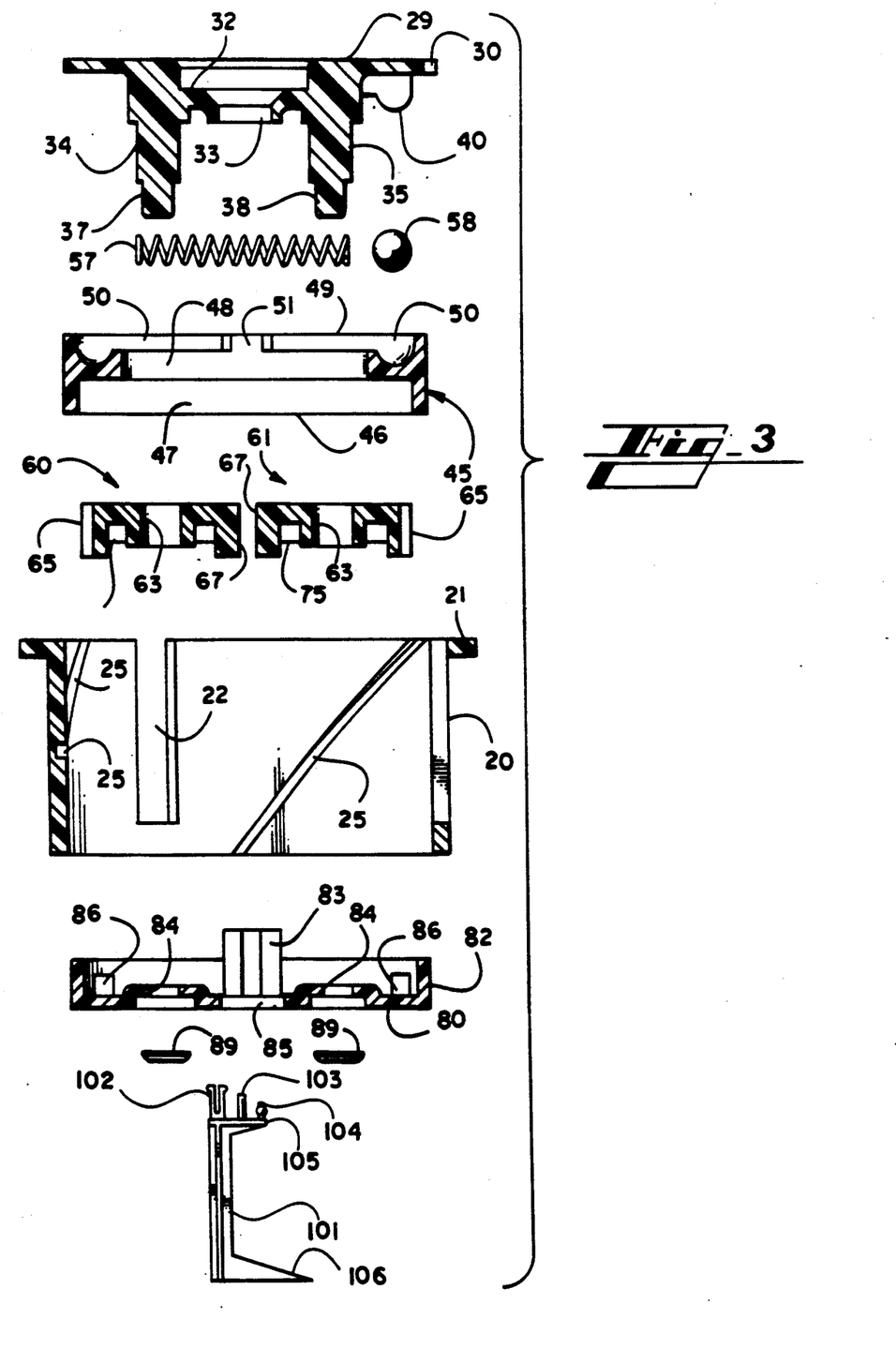
FIG. 3 is an exploded view of the elements of the apparatus shown in FIG. 1.
Figure 4:
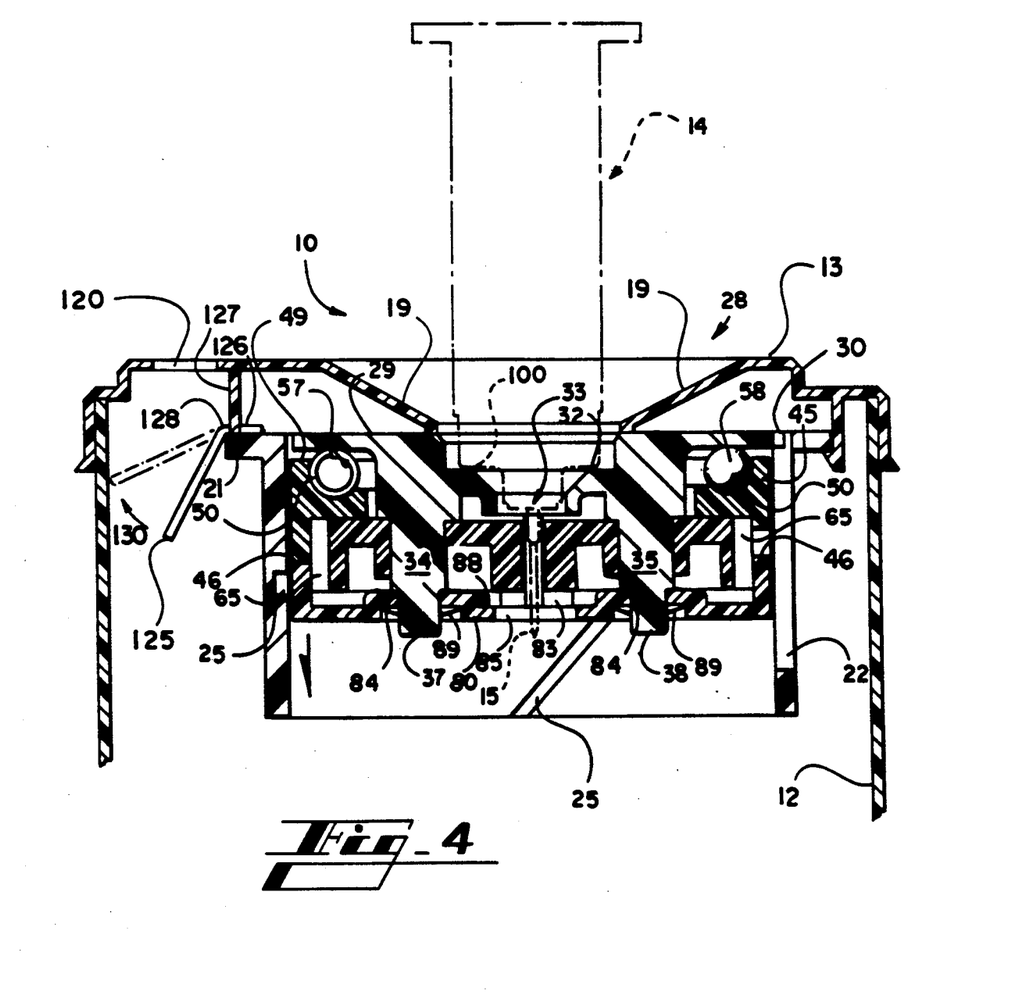
FIG. 4 is a vertical cross sectional view taken along line 4—4 of FIG. 1, with the cover in place.
Figure 5:
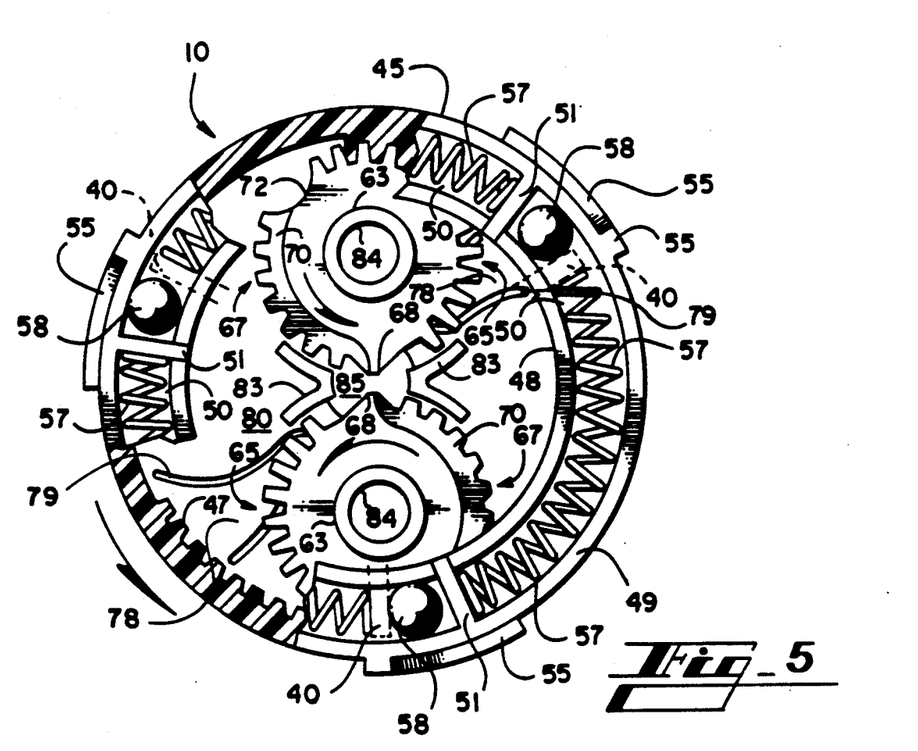
FIG. 5 is a top view of the apparatus of FIG. 1, with the carriage and actuator housing removed, and with parts broken away to show interior detail.
Figure 6:
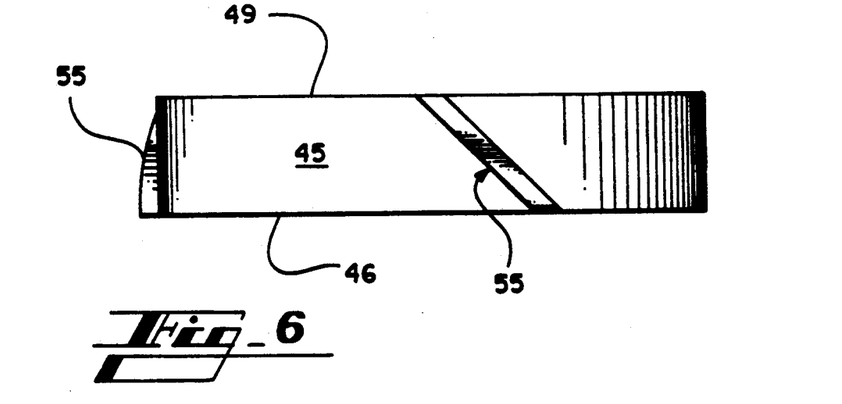
FIG. 6 is a side plan view of the circular drive gear.
Figure 7:
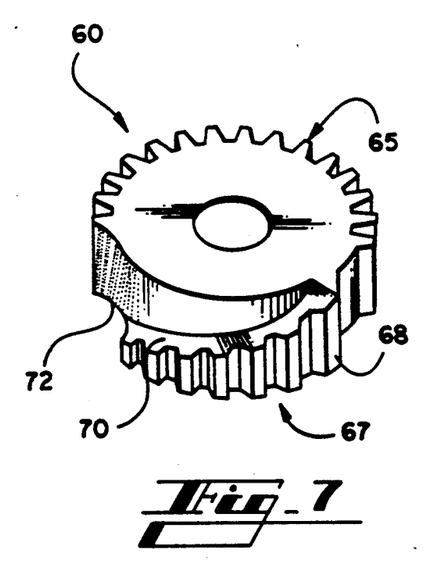
FIG. 7 is a pictorial view of one of the disconnect gears.
Figure 8:
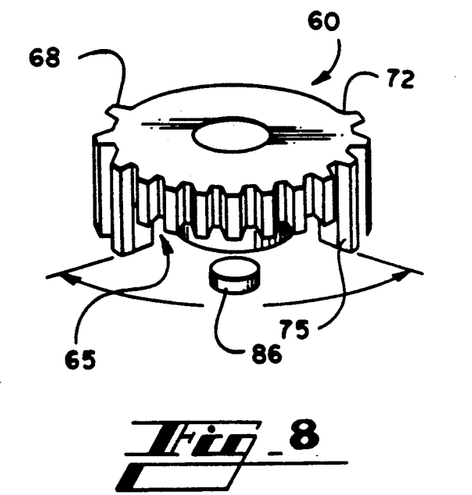
FIG. 8 is a pictorial view of the disconnect gear of FIG. 7, taken from the opposite side.
Figure 9:
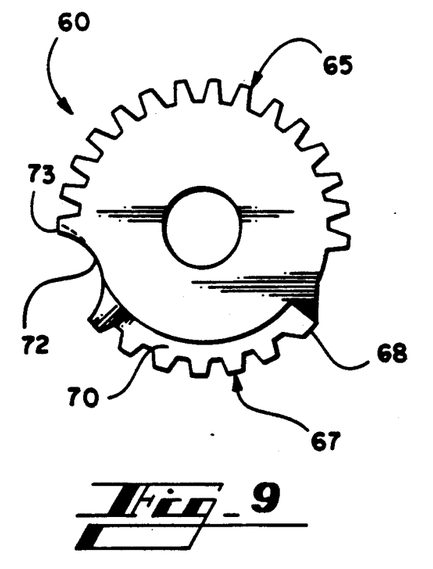
FIG. 9 is a top plan view of the gear shown in FIG. 7, showing the undercut cam surface.
Figure 10:
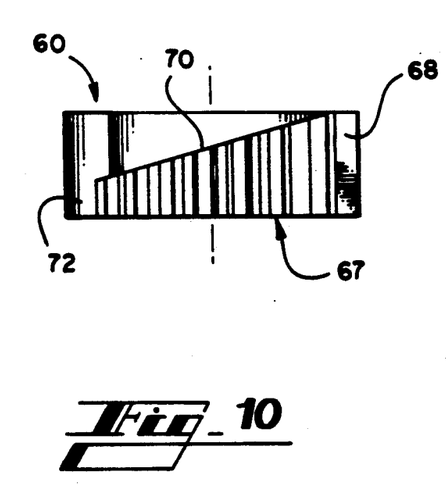
FIG. 10 is a side plan view of the gear shown in FIG. 9, showing the ramp profile.

Several other elements shown in FIG. 3 are connected to the carriage 28 and move with it within the actuator housing 20. A drive gear 45, also illustrated in FIG. 6, having a circular cross section fits around the gear shafts 34 and 35 and has a diameter slightly smaller than the inside diameter of the actuator housing 20, as shown in FIG. 4. The drive gear 45 defines an inner circular gear 47 adjacent the bottom surface 46 of the drive gear 45. A central bore 48 of diameter less than that of the circular teeth 47 is formed axially through the gear 45. In the annular space remaining, three arcuate spring tracks 50 are cut into the top surface 49 of the drive gear 45. These tracks 50 have a semicircular bottom profile which matingly receives the ends of the spring stop tabs 40 extending downwardly from the carriage 28. Narrow walls 51 formed between the spring tracks 50 act as spring compression actuators in the manner described below. Coil springs 57 are placed within the tracks 50 between one of the walls 51 and one of the stop tabs 40, as shown in FIG. 5. Three balls 58 of plastic, Teflon, stainless steel, or other material are also placed in each track 50 on the other side of each tab 40 from the spring 57. The purpose of the balls is to provide spacing and reduce friction between the drive gear 45 and the carriage 28. Those skilled in the art will understand that rounded nibs or projections extending from either element could provide these functions.

After the drive gear and springs are fitted under the carriage 28, a pair of needle disconnect or unscrewing gears 60 and 61 are rotatably journalled on the gear shafts 34 and 35. The structure of these gears is best shown in FIGS. 7-10. The shafts 34 and 35 are received through central bores 63. An outer series of teeth 65 mesh with the teeth 47 of the drive gear 45, as shown in FIG. 5, and provide about 115 degrees of rotation of the disconnect gears 60 and 61 about the shafts 34 and 35. Two separate inner series of teeth 67, one on each of the gears 60 and 61, face each other across the space below the insert opening 33. The teeth 67 are formed differently from the teeth 65 for the specific purpose of engaging and unscrewing the needle, as explained below. The series 67 begins with an alignment tooth 68. A ramp 70 is cut out of the gears 60 and 61 through the arc of the teeth 67, beginning at about the center of the alignment tooth 68 and sloping downwardly to meet a dropout opening 72, positioned in the embodiment shown about 115 degrees from the alignment tooth. As explained in more detail below, the ramp 70 accommodates portions of the needle assembly as it is unscrewed, and the dropout opening 72 allows the needle to drop vertically when it is fully unscrewed from the retainer 16. The dropout opening 72 includes an undercut cam surface 73. The undercut cam surfaces 73 of the gears 60, 61 act together to urge the needle into the container with a cam-like squeezing action after unscrewing, in those instances where the rubber sleeve abutting the threads interferes with the complete disengagement of the needle 15 from the syringe 14.

Figure 20:
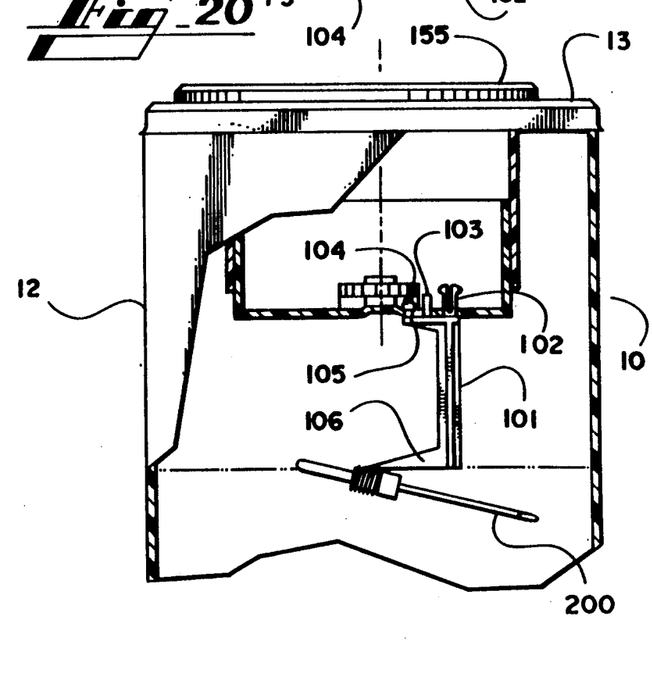
FIG. 20 is a cross-sectional side view of the needle removal apparatus, showing the locking function of the leg in its locked position.

The arcuate travel of the disconnect gears 60 and 61 is limited by rotation limiting cutouts 75 made in the lower portion of the outer series teeth 65. The ends of the cutouts 75 meet stops to be described below, and thereby stop motion of the gears when the dropout openings 72 are aligned with one another. As shown in FIG. 20 and described in detail below, when the accumulation of needles in the container 12 is such that further needles cannot be safely disposed, one of the cutouts 75 receives a locking tab 104 of a leg 101, which prevents rotation of the disconnect gears 60, 61. The arcuate length of the teeth 67 determines how many turns of the needle are made before the dropout opening is reached, and this arcuate length may be varied in accordance with the number of turns needed to release the needle from the particular locking device being used. For example, a luer lock may require only a portion of a turn, whereas a conventional screw connector may require about 1.5 to 2 turns. Also affected by the required number of turns is the length of the outer series of teeth 65, which may be constructed to provide more or less than the 115 degrees of rotation described above.

The needle removal apparatus 10 also includes a circular bottom plate 80, which includes an upwardly extending cylindrical wall 82 at the periphery of the plate 80. The bottom plate 80 defines a pair of openings 84 which receive the lock posts 37 and 38 at the ends of the shafts 34 and 35. A pair of flexible lock rings of conventional construction are forced onto the projecting lock posts to hold the bottom plate 80, and therefore the drive gear 45 and disconnect gears 60 and 61, in place beneath the carriage 28. In this configuration, shown in FIG. 4, a pair of V-shaped spacers 83 extend upwardly from the bottom plate to meet and support the housing 28 at the insert opening 33. These spacers also help to keep the needle in a relatively straight axial orientation as it is being inserted between the gears 60 and 61. A central opening 85 is formed in the bottom plate 80 below the insert opening 33, to allow disconnected needles to drop out of the apparatus.

A pair of stops 86 extend upwardly from the bottom plate into the rotation limiting cutouts 75 of the gears 60 and 61. The stops 86 are positioned so that they are engaged by the gears when the dropout openings 72 in the gears are aligned. The cylindrical wall 82 is dimensioned to extend up to engage the bottom of the drive gear 45, and positions the drive gear under the housing 28 without forcing the parts together so as to cause excess friction during rotation of the drive gear 45. A pair of spring tabs 78 with rebound blocks 88 attached thereto, both illustrated in FIG. 18, act to direct the carriage 28 upwardly towards the top of the actuator housing 20, after a user has released pressure from the retainer 16. The spring tabs 78 are formed in the flexible plastic material of the bottom plate 80 by cutouts 79, and the rebound blocks 88 are molded on the inward tip of the tabs. The blocks 88 are positioned to engage the gears 60 and 61. As the disconnect gears 60 and 61 complete their rotation, the spring tabs 78, which are cut out of the bottom plate 80, flex downwardly, and then, when pressure is released, rebound in an upward direction so as to urge the disconnect gears back towards the top of the actuator housing.

Figure 18:
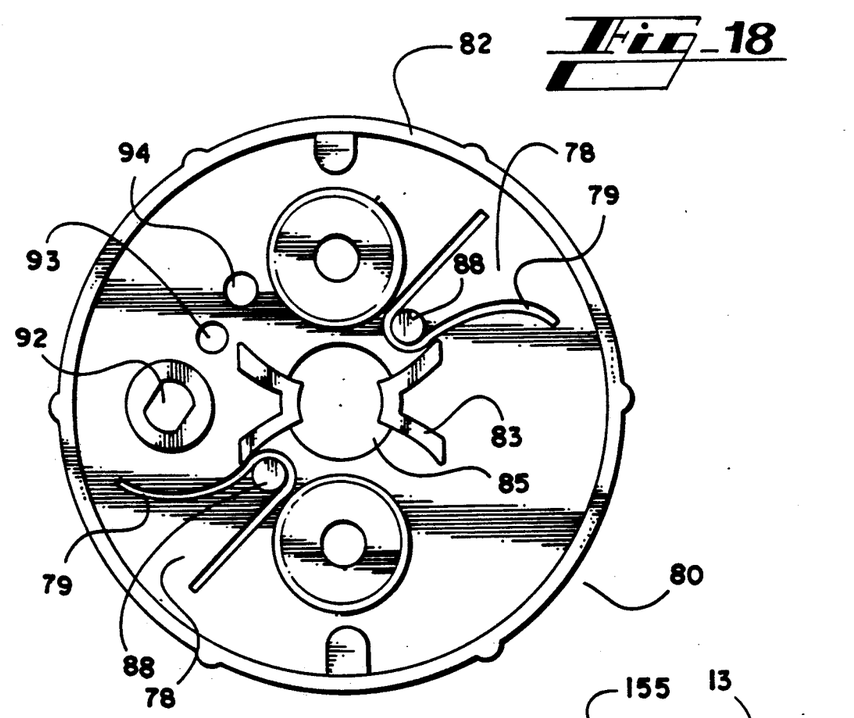
FIG. 18 is a bottom view of the bottom plate, showing the spring tabs.

Still referring to FIG. 3, the needle removal apparatus 10 also includes a locking leg 101, which includes three tabs 102, 103, 104, which extend upwardly from a top 105 of the leg 101 and selectively through the bottom plate 80. The bottom plate 80 includes three openings 92, 93, 94 for receiving the three tabs 102, 103, 104 of the leg 101, as illustrated in FIG. 18. Tab 102 has a split shape which facilitates easy snapping of tab 102 into opening 92. Tab 103, the centrally located of the three tabs, prevents the leg 101 from twisting. This function could also be accomplished by providing the tab 102 with a non-circular cross section. A foot 106 extends perpendicularly from the bottom of the leg 101.

Figure 19:
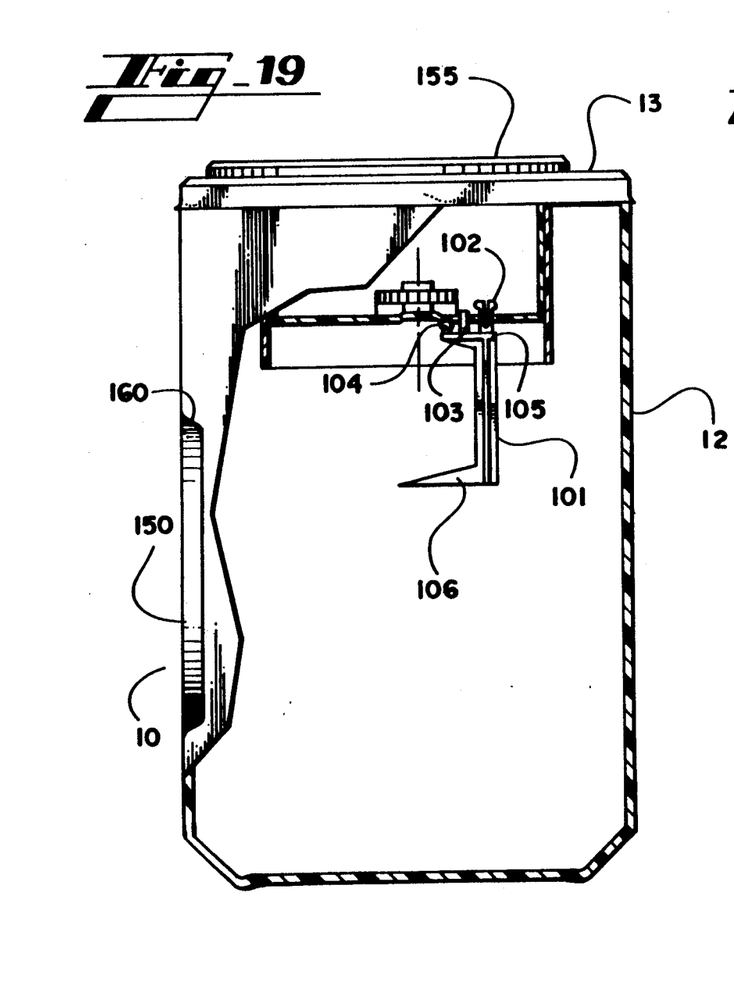
FIG. 19 is a cross-sectional side view of the needle removal apparatus, showing the leg in its normal, or unlocked, position.
Figure 21:
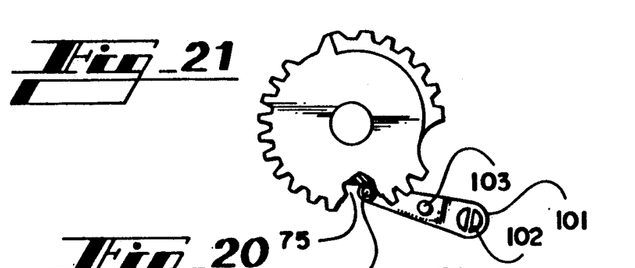
FIG. 21 is a diagrammatic top view of one of the disconnect gears, showing the way in which the leg locks in the cutout of the disconnect gear to prevent further disposal of needles.

As the disconnect gears 60 and 61 rotate and the carriage 28 moves downwardly through the actuator housing, the leg 101 and the foot portion 106 also move in a downward direction, towards the pile 200 of needles 15 which have been discarded in the container 12 as shown in detail in FIG. 19. When the size of the pile 200 of needles 15 in the container 12 is such that no additional needles may be safely discarded in the container 12 without risking escape of the needles through the insert opening 33 or having the point of a needle extend out of the insert opening 33, the locking tab 104 of the leg is positioned such that further movement of the disconnect gears is prevented, as shown in FIGS. 20 and 21.

Further details of the assembled configuration may be perceived from FIG. 5, which is a view downwardly into the apparatus with the carriage 28 removed. A vertical space for receiving the needle is bounded by the two disconnect gears 60 and 61, and the two spacers 83.

Figure 24:
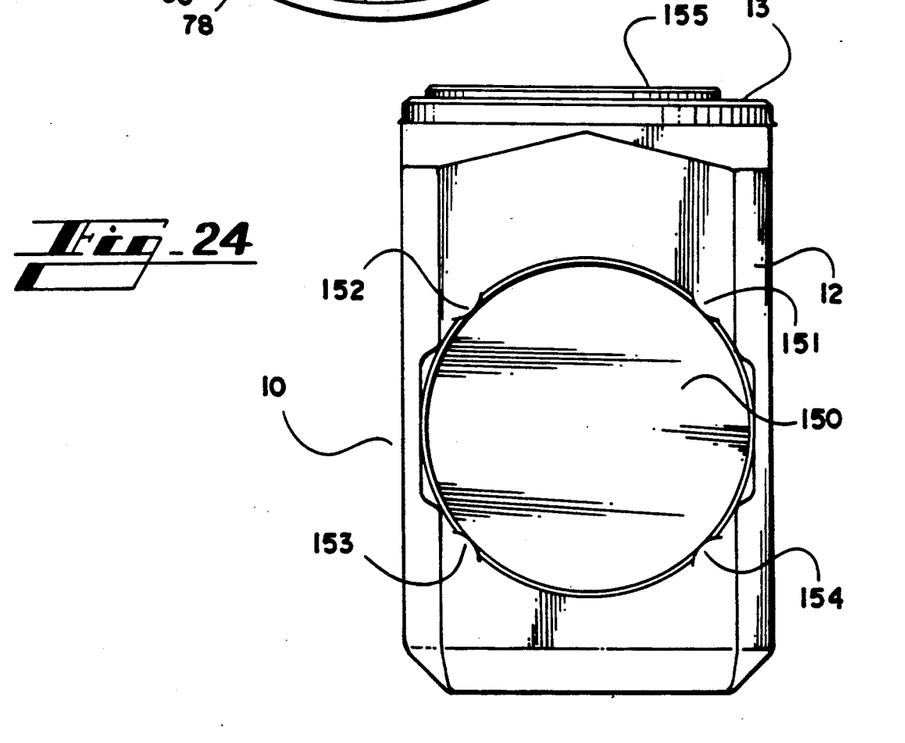
FIG. 24 is a side view of the needle removal apparatus, showing the mounting of the permanent lid to the container.

The needle removal apparatus is intended to be disposable after a period of use, such as when the container 12 is full. Thus, all of the elements described above are preferably made of suitable plastics known to those skilled in the art, although metal can be utilized where appropriate. A permanent lid 150 is attached to one side of the container 12, as illustrated in FIG. 24. The lid 150 sits in a recess 160, seen in part in FIG. 19, in the container 12, and is held in place by four tabs 151, 152, 153, 154. When the container 12 reaches its safe limit of needles 200 and the leg 101 locks the disconnect gears 60 and 61, the permanent lid 150 may be placed over a raised portion of the cover 155 under which the carriage 28 is positioned, thus safely sealing the insert opening 33 of the container 12. The entire container 12 may then be safely disposed.

The needle removal apparatus 10 is constructed to accommodate needles other than the types attached to syringes. A coat hanger-shaped opening 120 in the raised portion 155 of the cover 13 is large enough to receive numerous varieties of non-syringe needles, including the so-called "butterfly" needle used by hospital personnel, as FIG. 4 shows. A hinged retaining flap 125 is mounted between the cover 13 and the annular plate 29. A strut 127, extending downward from the cover 13 and abutting the plate 29, passes through a hole 126 in the flap, thus positioning the flap 125. The flap 125 includes a hinged portion 128, around which the flap is rotatable. The retaining flap 125 is positioned so as to not impede the disposal of non-syringe needles down into the opening 120 when the apparatus 10 is in an upright position on a hospital personnel's medical cart (not pictured). However, if the apparatus 10 is upset from its upright position, the flap 125 pivots around its hinge 128 in the direction of the arrow 130 to cover the opening 120, thus preventing disposed contaminated needles from spilling out of the apparatus 10. It should also be noted that the detaching mechanism of each model of the needle removal apparatus 10 can accommodate only one particular brand of needles, due to the various threading mechanisms employed by each manufacturer of syringe-held needles. Accordingly, the opening 120 also includes two teeth-like elements 121, 122 which can be used to unscrew needles not suited to the particular model of the needle removal apparatus which the personnel are currently using.

Figure 23:
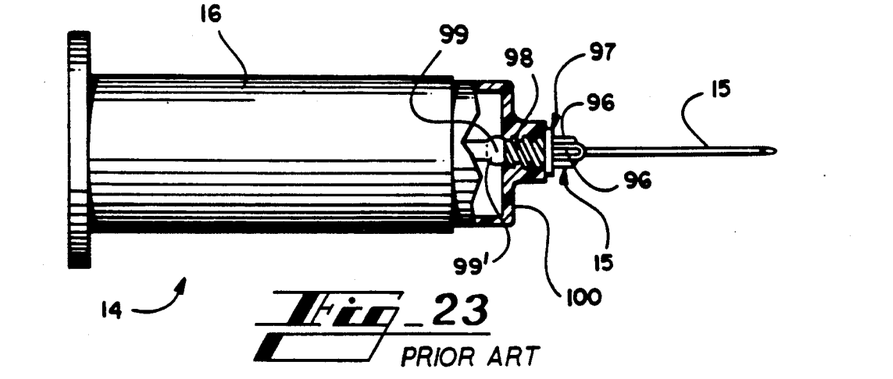
FIG. 23 is a side view of a prior art syringe assembly with portions broken away.

Further details of the construction of a typical conventional syringe assembly 14 are shown in FIG. 23. The needle 15 extends into a collar 95, which defines a plurality of outwardly extending flanges 96. The flanges terminate in a circular stop 97, which separates them from a threaded screw portion 98. The collar 95 is screwed into a tapped hole in the retainer portion 16 of the syringe 14, with an inner needle 99 (shown covered by a protective envelope) extending into the retainer 16. The protective envelope often terminates in a raised ring 99' adjacent to the threads 98. The ring 99' may become caught in the disconnect gears even after the threads 98 are separated from the syringe. The flanges 96 are provided to allow the user to get a grip on the needle for screwing and unscrewing the needle. It is the object of the present invention to obviate the need for grasping the collar by hand to unscrew it after the needle is contaminated. The retainer portion 16 includes a leading surface 100, which engages the annular shoulder 32 within the carriage 28.

Figure 11:
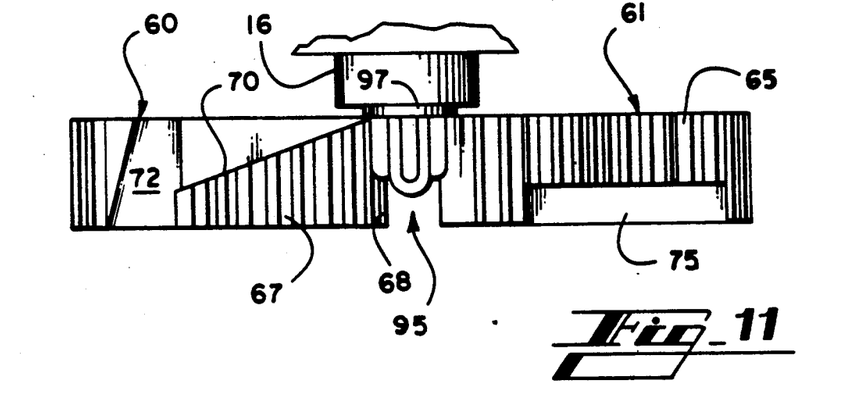
FIG. 11 is a diagrammatic side view of the disconnect gears and a needle initially inserted into engagement with the gears.
Figure 12:
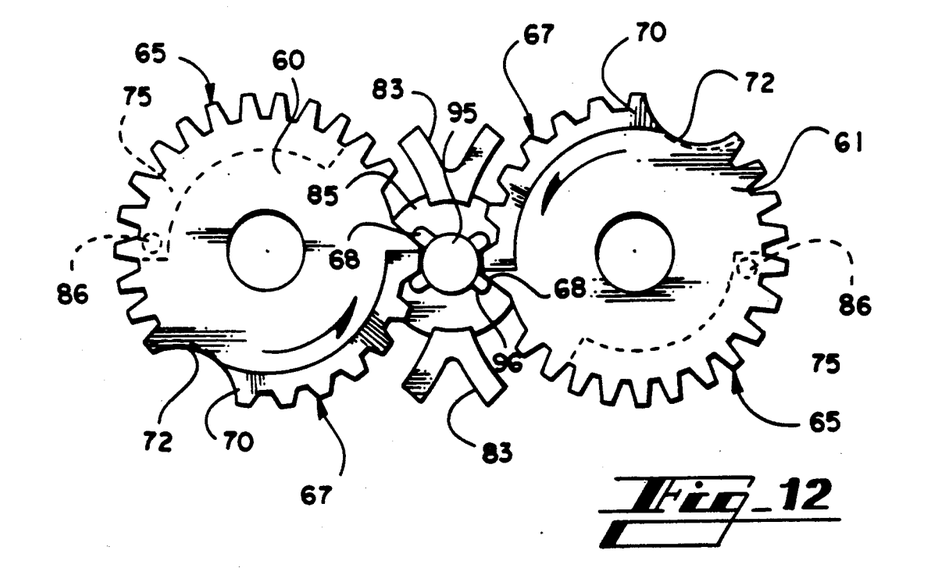
FIG. 12 is a diagrammatic top view of the situation shown in FIG. 11.

Operation of the needle removal apparatus is described as follows, with particular reference to FIGS. 11-17, which show a sequence of positions of the disconnect gears 60 and 61 during operation. After the syringe assembly 14 has been used and the needle 15 contaminated, the user simply takes the needle retainer 16 in one hand and inserts it into the carriage 28, until the needle 15 passes into the space between the disconnect gears, and the leading surface 100 of the retainer 16 is in contact with the annular shoulder 32. At this point, the flanges 96 have engaged the alignment teeth 68 of both gears 60 and 61, and have been caused to align the syringe so that the flanges are astride the alignment teeth as shown in FIGS. 11 and 12. The position of the syringe at this point in the operation is shown in dotted lines in FIG. 4.

Figure 13:
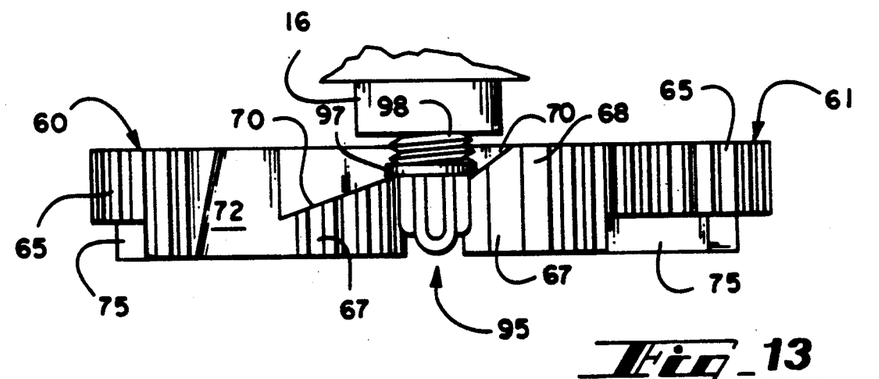
FIG. 13 is a diagrammatic side view of the same needle pushed further into the apparatus between the disconnect gears.

Detachment of the needle 15 from the retainer 16 is accomplished when the user asserts downward pressure on the retainer. This pressure causes the carriage 28 to begin to move downwardly along the slots 22 in the actuator housing 20. As this occurs, the cam followers 55 of the drive gear 45 are forced to follow the path defined by the cam tracks 25 of the actuator housing 20. Thus, the drive gear 45 rotates counterclockwise as it descends with the carriage 28, and its rotation causes the following other functions to be carried out. The rotating inner teeth 47 cause rotation of the disconnect gears 60 and 61, in turn causing the inner unscrewing teeth 67 to move relative to the flanges 96 of the needle collar 95. The teeth 67 engage the flanges 96 and turn the collar in an unscrewing direction (clockwise looking down as in FIGS. 12 and 15) as the gears turn. After a portion of the permitted rotation, the needle collar position is shown in FIG. 13. The threaded portion 98 has begun to emerge from the needle retainer 16. The ramp 70 provides room for the circular stop 97 to move downwardly past the gears, while the flanges remain engaged with the inner unscrewing teeth 67.

As the drive gear 45 rotates, it causes the spring compression walls 51 to compress the return springs 57 against the spring stops 40, which do not rotate. In the embodiment shown in FIG. 5, the springs are compressed through about 53 degrees of arc. At the same time, the balls 58 roll between the carriage 28 and the spring tracks 50, in the space created by the departure of the adjacent wall 51 from its rest position.

Figures 14, 15:
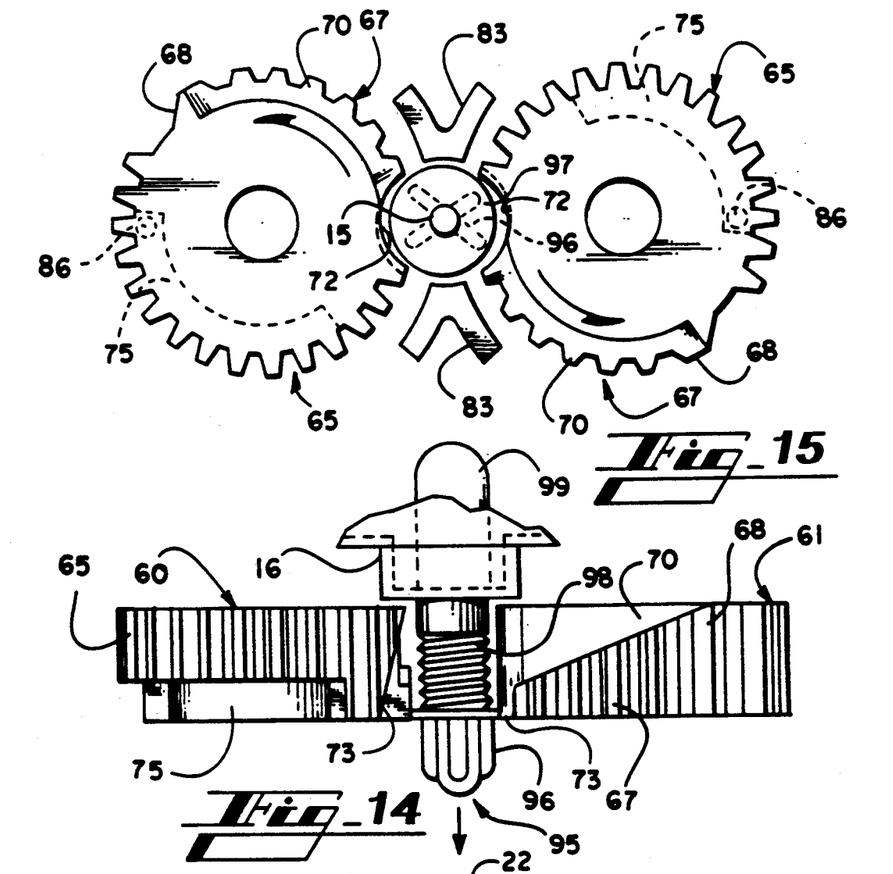
FIG. 14 is a diagrammatic side view of the same needle pushed far enough into the apparatus to disconnect the needle from the needle retainer.
FIG. 15 is a diagrammatic top view of the situation shown in FIG. 14.
Figure 16:
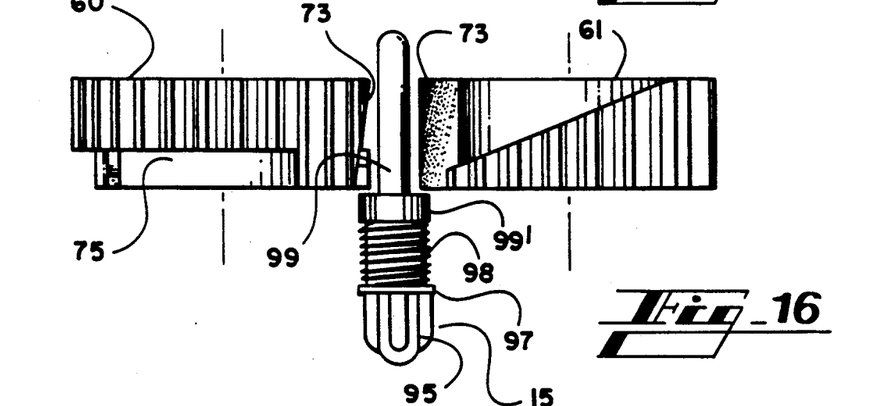
FIG. 16 is a diagrammatic side view of the same needle, urged completely through the apparatus by the undercut cam surfaces.

When the rotation of the disconnect gears 60 and 61 has reached the configuration shown in FIGS. 14 and 15, the threaded portion 98 of the collar 95 has been completely unthreaded from the retainer 16, and the collar has moved down the ramp 70 into the dropout openings 72, which are now aligned across from one another. Thus, there should be nothing to prevent the needle assembly from falling down through the opening 85 in the bottom plate, into the container 12.

In certain situations, the threaded portion 98 of the collar 95 will be completely unthreaded, as shown in FIGS. 14 and 15, but a portion of the needle assembly 15, such as the ring 99' of the protective envelope of FIG. 23, will obstruct passage of the needle assembly 15 into the container 12. When such blockage occurs, the cutout cam surfaces 73 are urged against the needle assembly 15 in such a manner so as to force the needle assembly 15 to fall into the container 12, as fully shown in FIGS. 16 and 17. The cutout cam surfaces 73 thus prevent detached contaminated needles which are "trapped" between the disconnect gears from spilling away from the container and causing a potential health hazard, or from interfering with further operation of the detaching mechanism.

The ending position of the gears 60 and 61 is defined by the posts 86 on the bottom plate 80, which strike the ends of the cutouts 75 in the gears and prevent further rotation. This also prevents further penetration of the carriage, drive gear, and bottom plate into the actuator housing.

At this time, the user may terminate downward pressure on the needle retainer 16 and withdraw it from the apparatus 10. The energy stored in the compressed return springs 57 causes the drive gear 45 to rotate in the opposite direction to its original position. The cam followers 55 climb back up the cam tracks 25, and the carriage 28 moves up the slots 22. The apparatus stops rotating, and reaches its original orientation as the balls 58 become trapped between the stops 40 and the walls 51. The alignment teeth 68 of the gears 60 and 61 are now reset across from one another ready to receive the next needle collar.

Figure 17:
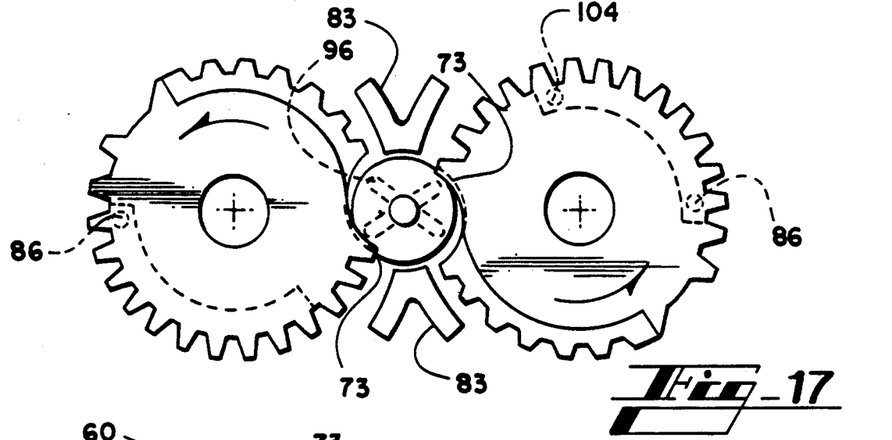
FIG. 17 is a diagrammatic top view of the situation shown in FIG. 16.

When a sufficient quantity of needles 200 have been disposed in the container 12, the apparatus 10 can no longer function safely without creating a risk that needles will protrude through the openings 33 and 85 into which they are placed for disposal. During the downward movement of the carriage 28 and the leg 101, if the foot portion 106 of the leg 101 encounters the pile 200 of needles 15, the tabs 102, 103, and 104 of the leg 101 are pushed further upward through the openings 92, 93, and 94 and closer to the gears 60 and 61. After the gears 60 and 61 have been sufficiently rotated to unthread the needle 15 from the retainer 16, as shown in FIGS. 14 and 15, the locking tab 104, due to the upward movement caused by the foot portion 106 encountering the pile 200 of needles 15, moves into the cutout 75 of one of the disconnect gears. Thereafter, when the gears 60 and 61 strike the posts 86 and begin to return to their initial position, the end of the cutout 75 will encounter the locking tab 104 and the gears 60 and 61 will be unable to move in either direction. The engagement of the tab 104 with the cutout 75 is shown in FIG. 21, and the relative positions of the post 86 and the tab 104 when locking occurs are shown in FIG. 17. Therefore, further operation of the actuator housing 20 is prevented and the apparatus 10 is rendered inoperative.

If the needle collar has not been fully screwed into the retainer, the circular stop 97 may engage the top of the gears 60 and 61 before the leading surface 100 meets the annular shoulder 32 of the carriage. In this case, the spring tabs 78 will allow the gears to yield downwardly, so that the flanges will still engage the teeth 68 and the retainer will transmit pressure to the carriage.

It should be understood that the return function provided by the return springs 57 could be performed by compression springs mounted below the bottom plate 80 to urge the assembled parts upwardly when pressure is released. It should also be understood that the needle collar could be engaged for unscrewing by means other than gear teeth. For example, the disconnect gears could be wheels having resilient outer bands for frictionally engaging the needle and/or the interior of the drive gear, which could also be lined with a high friction interface rather than gear teeth. Alternately, the needle collar could be rotated by a rack or racks caused to move past the collar.

While this invention has been described in detail with particular reference to preferred embodiments thereof, it will be understood that variations and modifications can be effected within the spirit and scope of the invention as described hereinbefore and as defined in the appended claims.

What is claimed is:

1. An apparatus for removing needles of the type received in syringe bodies, comprising:
    means for disengaging said needle from said syringe body;
    a container associated with said disengaging means, for confining said needle after disengagement from said syringe body; and
    means responsive to an accumulation of said needles in said container for preventing disengagement of additional needles.

2. The apparatus of claim 1, wherein said disengaging means moves downwardly into said container during disengagement of said needles, and wherein said disengagement prevention means comprises a leg mounted to and extending downwardly from said disengaging means.

3. The apparatus of claim 2, wherein said disengaging means comprises:
    a carriage defining an insert opening for receiving said needles;
    means for movably supporting said carriage; and
    means drivingly linked to said carriage and driven by force exerted on said carriage parallel to the length of said needle for rotating said needle when said needle is received in said insert opening, such that said needle is released from said syringe.

4. The apparatus of claim 3, wherein said needle includes a plurality of flanges extending outwardly from said collar, and wherein said means for rotating said needle comprises:
    at least one disconnect gear rotatably mounted adjacent to said insert opening with gear teeth facing said insert opening, said teeth positioned for engaging said needle flanges, said gear defining a ramp cut into said gear teeth in the path of said needle flanges around a portion of the periphery of said disconnect gear, said ramp terminating in a discharge opening; and
    means for rotating said gear in a disconnect direction responsive to downward movement of said needle into said insert opening.

5. The apparatus of claim 4, wherein said means for rotating said needle comprises a pair of disconnect gears, each defining an undercut cam surface positioned to engage said needle following engagement of said needle by said gear teeth and to urge said needle through said insert opening and into said container as said gears are rotated in a disconnect direction.

6. The apparatus of claim 3, wherein said carriage is mounted for movement along a path parallel to the axis of said insert opening.

7. The apparatus of claim 2, wherein said leg is mounted for movement with respect to said disengaging means and includes at least one tab extending upwardly from a first position outside said disengaging means to a second position wherein said tab is within said disengaging means.

8. The apparatus of claim 7, further comprising means, within said disengaging means and responsive to said leg encountering an accumulation of said needles in said container, for engaging said tab in said second position so as to disable said disengaging means.

9. The apparatus of claim 8, wherein said leg includes a foot portion extending substantially perpendicularly from a bottom portion of said leg.

10. The apparatus of claim 1, further comprising means for receiving needles of a type which cannot be safely disengaged by said disengaging means.

11. The apparatus of claim 10, wherein said receiving means comprises an opening in a cover portion of said container.

12. The apparatus of claim 11, wherein said opening is substantially triangular in shape.

13. The apparatus of claim 12, wherein said opening includes means for disconnecting needles.

14. The apparatus of claim 13, wherein said disconnecting means includes at least one tooth-shaped element extending into said opening.

15. The apparatus of claim 1, wherein said container includes a recess for storing a permanent lid, such that when said disengagement prevention means prevents disengagement of additional needles, said permanent lid may be positioned over said disengaging means and said container may be safely disposed.

16. An apparatus for removing needles of the type received in syringe bodies by way of a rotating connector, and defining outwardly extending flanges positioned outside said syringe body, comprising:
    a container for confining said needles after removal from said syringe bodies;
    a cylindrical actuator housing defining a cam track in the cylindrical wall thereof;
    a carriage defining an insert opening along the axis of said actuator housing for receiving said needle, said carriage being mounted for sliding movement axially within said actuator housing;
    a pair of disconnect gears rotatably mounted on said carriage about axes parallel to the axis of said actuator housing, with the peripheral teeth of said gears passing closely adjacent to opposite sides of said insert opening so as to engage said needle flanges when said needle is inserted, each of said gears defining a ramp cut into said gear teeth in the path of said needle flanges around a portion of the periphery of said disconnect gear, said ramp terminating in a discharge opening;
    a circular drive gear surrounding said disconnect gears, said drive gear defining a cam follower engaging said cam track in said actuator housing;
    said cam track causing said drive gear to rotate upon motion of said carriage into said actuator housing thereby causing rotation of said disconnect gears so as to rotate said needle and disconnect it from said syringe body;
    means for rotating said drive gear in the opposite direction to return said disconnect gears to their original orientation and to move said carriage to its original position;

means responsive to an accumulation of said needles in said container for preventing disengagement of additional needles, comprising a leg mounted to and extending downwardly from said actuator housing; and means for receiving needles of the type which cannot be safely disconnected, comprising a substantially triangular opening in a cover portion of said container, said opening including at least one tooth-like element for disconnecting needles.

17. A method of manually removing a needle from a syringe body to which the needle is attached by a rotating connector, comprising the steps of:

inserting said needle into an opening in a movably supported carriage and engaging said syringe body against said carriage;

moving said carriage by exerting pressure upon said syringe body and thereby against said carriage;

driving said needle in a rotating motion by drivingly linking said movement of said carriage to a means for rotating said needle, said rotating motion being sufficient to release said needle from said syringe body such that said needle falls into a container for confining said needle; and disabling movement of said carriage responsive to an accumulation of needles in said container.

18. A manually-operated apparatus for one-handed removal of needles of the type received in syringe bodies by way of a rotating connector, and defining a collar positioned outside said syringe body, comprising:

a carriage defining an insert opening for receiving said needle;

means for movably supporting said carriage;

means drivingly linked to said carriage and driven by force exerted on said guide housing parallel to the length of said needle for engaging said collar and rotating said needle when said needle is received in said insert opening, such that said needle is released from said syringe;

a container for confining said needle after release from said syringe body; and means responsive to an accumulation of said needles in said container for preventing disengagement of additional needles, comprising a leg mounted to and extending downwardly from said actuator housing.

19. The apparatus of claim 18, further comprising means for receiving needles of a type which cannot be safely disengaged by said disengaging means.

20. The apparatus of claim 19, wherein said receiving means comprises an opening in a cover portion of said container.

21. The apparatus of claim 20, wherein said opening is substantially triangular in shape.

22. The apparatus of claim 21, wherein said opening includes means for disconnecting needles.

23. The apparatus of claim 22, wherein said disconnecting means includes at least one tooth-shaped element extending into said opening.

24. The apparatus of claim 18, wherein said container includes a recess for storing a permanent lid, such that when said disengagement prevention means prevents disengagement of additional needles, said permanent lid may be positioned over said disengaging means and said container may be safely disposed.

25. An apparatus for removing needles of the type received in syringe bodies by way of a rotating connector, and defining a collar positioned outside said syringe body, comprising:

a carriage mounted for movement within an actuator housing and defining an insert opening for receiving said needle;

a container for confining said needles;

means positioned adjacent to said insert opening for rotating said needle responsive to movement of said carriage with respect to said actuator housing, comprising a pair of disconnect gears rotatably mounted on said carriage with their peripheries on opposite sides of said insert opening and means for rotating said disconnect gears responsive to downward movement of said needle into said insert opening; and means responsive to an accumulation of a predetermined number of said needles in said container for preventing disengagement of additional needles, comprising a leg removably mounted to and extending downwardly from said actuator housing.

26. The apparatus of claim 25, wherein said means for rotating said disconnect gears comprises:

a cam track defined in the cylindrical wall of said actuator housing;

a circular drive gear engaging said disconnect gears, said drive gear defining a cam follower;

said cam follower engaging said cam track in said actuator housing; and said cam track causing said drive gear to rotate upon motion of said carriage into said actuator housing, thereby causing rotation of said disconnect gears so as to rotate said needle and disconnect it from said syringe body.

27. The apparatus of claim 26, further comprising means for receiving needles of a type which cannot be safely disengaged by said disengaging means.

28. The apparatus of claim 27, wherein said receiving means comprises an opening in a cover portion of said container.

29. The apparatus of claim 28, wherein said opening is substantially triangular in shape.

30. The appartus of claim 29, wherein said opening includes means for disconnecting needles.

31. The apparatus of claim 30, wherein said disconnecting means includes at least one tooth-shaped element extending into said opening.

32. The apparatus of claim 25, wherein said container includes a recess for storing a permanent lid, such that when said disengagement prevention means prevents disengagement of additional needles, said permanent lid may be positioned over said disengaging means and said container may be safely disposed.

33. An apparatus for removing needles of the type received in syringe bodies, comprising:

a container for confining said needle after removal; and means for disengaging said needle from said syringe body, comprising a pair of rotatable disconnect gears, each defining an undercut cam surface, said cam surfaces positioned so as to cooperate with one another and urge said needle into said container when said disconnect gears are rotated.

* * * * *